(12) United States Patent
Stark

(10) Patent No.: US 9,314,938 B2
(45) Date of Patent: *Apr. 19, 2016

(54) PRESERVATION OF WOOD, COMPOSITIONS AND METHODS THEREOF

(71) Applicant: Apinee, Inc., Roseville, MN (US)

(72) Inventor: Joseph L. Stark, Minneapolis, MN (US)

(73) Assignee: Apinee, Inc., Roseville, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/176,339

(22) Filed: Feb. 10, 2014

(65) Prior Publication Data

US 2014/0154419 A1 Jun. 5, 2014

Related U.S. Application Data

(63) Continuation of application No. 13/142,976, filed as application No. PCT/US2009/069802 on Dec. 30, 2009, now Pat. No. 8,691,340.

(60) Provisional application No. 61/141,920, filed on Dec. 31, 2008.

(51) Int. Cl.
*B27K 3/15* (2006.01)
*B27K 3/08* (2006.01)
*A01N 25/30* (2006.01)

(52) U.S. Cl.
CPC . *B27K 3/08* (2013.01); *A01N 25/30* (2013.01); *B27K 3/15* (2013.01)

(58) Field of Classification Search
None
See application file for complete search history.

(56) References Cited

U.S. PATENT DOCUMENTS

| | | |
|---|---|---|
| 2,006,207 A | 6/1935 | Bhagwat |
| 2,079,626 A | 5/1937 | Ashby et al. |
| 2,717,423 A | 9/1955 | Murray, Jr. et al. |
| 2,962,459 A | 11/1960 | Ash et al. |
| 3,006,784 A | 10/1961 | Ryan et al. |
| 3,083,170 A | 3/1963 | Booty |
| 3,196,494 A | 7/1965 | Hoffmann et al. |
| 3,215,596 A | 11/1965 | Johnson et al. |
| 3,219,473 A | 11/1965 | Dimond |
| 3,322,318 A | 5/1967 | Turner et al. |
| 3,356,622 A | 12/1967 | Delmonte |
| 3,462,237 A | 8/1969 | Sellet |
| 3,468,822 A | 9/1969 | Wismer et al. |
| 3,491,067 A | 1/1970 | Sellet |
| 3,559,920 A | 2/1971 | Moore |
| 3,627,719 A | 12/1971 | Sellet |
| 3,644,171 A | 2/1972 | Bevan et al. |
| 3,674,415 A | 7/1972 | Sellet |
| 3,698,931 A | 10/1972 | Horowitz |
| 3,705,777 A | 12/1972 | Witkowski |
| 3,706,619 A | 12/1972 | Freeman |
| 3,713,879 A | 1/1973 | Wu |
| 3,737,488 A | 6/1973 | Porter et al. |
| 3,740,337 A | 6/1973 | Sommers |
| 3,847,857 A | 11/1974 | Haag et al. |
| 3,906,127 A | 9/1975 | Hollmann et al. |
| 3,915,919 A | 10/1975 | Nishioka et al. |
| 3,935,341 A | 1/1976 | Sorensen et al. |
| 3,935,467 A | 1/1976 | Gablin |
| 3,950,218 A | 4/1976 | Levesque |
| 3,964,385 A | 6/1976 | Knight |
| 3,965,047 A | 6/1976 | Yamaguchi |
| 3,968,276 A | 7/1976 | Allen |
| 3,993,721 A | 11/1976 | Soda et al. |
| 4,010,163 A | 3/1977 | Hesse et al. |
| 4,018,642 A | 4/1977 | Pike et al. |
| 4,026,847 A | 5/1977 | Ripa et al. |
| 4,040,823 A | 8/1977 | Yamaguchi |
| 4,048,101 A | 9/1977 | Nakamachi et al. |
| 4,081,414 A | 3/1978 | Abe et al. |
| 4,104,357 A | 8/1978 | Blair |
| 4,114,333 A | 9/1978 | Jones et al. |
| 4,115,178 A | 9/1978 | Cone et al. |
| 4,128,689 A | 12/1978 | Heaps et al. |
| 4,129,533 A | 12/1978 | Moore, Jr. |
| 4,141,944 A | 2/1979 | Anstadt et al. |
| 4,195,880 A | 4/1980 | Henkhaus |
| 4,230,600 A | 10/1980 | Bornstein |
| 4,230,822 A | 10/1980 | Murch et al. |
| 4,234,326 A | 11/1980 | Bailey et al. |
| 4,237,182 A | 12/1980 | Fulmer et al. |

(Continued)

FOREIGN PATENT DOCUMENTS

| | | |
|---|---|---|
| CA | 1 125 764 | 6/1982 |
| CA | 1 141 099 | 2/1983 |

(Continued)

OTHER PUBLICATIONS

Attwood, D. and Florence, A.T., *Surfactant Systems Their chemistry, pharmacy and biology* (1983), (cover page, publication page, and pp. 1-11).

Materials Research Society Symposium Proceedings vol. 124, Microwave Processing of Materials held Apr. 5-8, 1988, *Microwave Processing of Polymers and Biomass Materials* by George et al. (cover page, publication page, pp. 189-194).

Materials Research Society Symposium Proceedings vol. 430, Microwave Processing of Materials V, Symposium held Apr. 8-12, 1996, *Monitoring Resin Cure of Medium Density Fiberboard using Dielectric Sensors* by R.J. King and R.W. Rice (cover page, publication page, table of contents page v, and pp. 601-605).

(Continued)

*Primary Examiner* — Erma Cameron
(74) *Attorney, Agent, or Firm* — Merchant & Gould P.C.

(57) ABSTRACT

The disclosure relates to compositions for wood preservation and methods of applying compositions for wood preservation. The compositions comprise nonionic surfactant mixtures and prepolymer. Compositions of nonionic surfactant mixtures and prepolymers can be used advantageously in methods to preserve wood by impregnation of the wood with preservatives at ambient atmospheric pressures.

8 Claims, No Drawings

(56) References Cited

U.S. PATENT DOCUMENTS

| | | |
|---|---|---|
| 4,244,901 A | 1/1981 | Wencley et al. |
| 4,252,857 A | 2/1981 | Heine et al. |
| 4,258,088 A | 3/1981 | Cone et al. |
| 4,264,760 A | 4/1981 | Meyer |
| 4,265,963 A | 5/1981 | Matalon |
| 4,357,377 A | 11/1982 | Yamamoto |
| 4,374,687 A | 2/1983 | Yamamoto |
| 4,382,884 A | 5/1983 | Berini et al. |
| 4,399,195 A | 8/1983 | Allen, Sr. |
| 4,403,013 A | 9/1983 | Robitschek et al. |
| 4,425,998 A | 1/1984 | Hof et al. |
| 4,430,468 A | 2/1984 | Schumacher |
| 4,433,031 A | 2/1984 | Allen, Sr. |
| 4,433,120 A | 2/1984 | Chiu |
| 4,439,070 A | 3/1984 | Dimmick |
| 4,443,520 A | 4/1984 | Braithwaite, Jr. |
| 4,515,739 A | 5/1985 | Maine |
| 4,545,597 A | 10/1985 | Meatto et al. |
| 4,559,162 A | 12/1985 | Abel et al. |
| 4,582,758 A | 4/1986 | Bruce et al. |
| 4,595,710 A | 6/1986 | Albertelli et al. |
| 4,609,690 A | 9/1986 | Gruber et al. |
| 4,649,793 A | 3/1987 | Blackshear et al. |
| 4,652,393 A | 3/1987 | Ely et al. |
| 4,661,382 A | 4/1987 | Cooke |
| 4,714,577 A | 12/1987 | Nagamoto et al. |
| 4,743,633 A | 5/1988 | Navratil et al. |
| 4,777,987 A | 10/1988 | Asagi et al. |
| 4,780,988 A | 11/1988 | Mielke et al. |
| 4,810,741 A | 3/1989 | Kim |
| 4,818,590 A | 4/1989 | Prince et al. |
| 4,852,314 A | 8/1989 | Moore, Jr. |
| 4,871,594 A | 10/1989 | Bister et al. |
| 4,992,481 A | 2/1991 | von Bonin et al. |
| 5,021,122 A | 6/1991 | Desrochers et al. |
| 5,026,530 A | 6/1991 | Drinkard, Jr. et al. |
| 5,055,410 A | 10/1991 | Blumenthal et al. |
| 5,060,291 A | 10/1991 | Albertelli |
| 5,074,946 A | 12/1991 | Daisy |
| 5,075,052 A | 12/1991 | Malvassora |
| 5,086,084 A | 2/1992 | Michaelson |
| 5,091,240 A | 2/1992 | Kajander et al. |
| 5,115,609 A | 5/1992 | Sing |
| 5,135,612 A | 8/1992 | Desrochers et al. |
| 5,139,861 A | 8/1992 | Williams et al. |
| 5,162,394 A | 11/1992 | Trocino et al. |
| 5,202,150 A | 4/1993 | Benson et al. |
| 5,218,793 A | 6/1993 | Ball |
| 5,228,905 A | 7/1993 | Grunewalder et al. |
| 5,245,812 A | 9/1993 | Landers |
| 5,247,005 A | 9/1993 | von Bonin et al. |
| 5,290,602 A | 3/1994 | Argyropoulos et al. |
| 5,296,176 A | 3/1994 | Nakamura |
| 5,299,400 A | 4/1994 | Sing |
| 5,303,720 A | 4/1994 | Banerjee et al. |
| 5,318,844 A | 6/1994 | Brandon |
| 5,320,891 A | 6/1994 | Levy et al. |
| 5,344,493 A | 9/1994 | Jackson |
| 5,351,847 A | 10/1994 | Greenbaum |
| 5,362,519 A | 11/1994 | Argyropoulos et al. |
| 5,368,794 A | 11/1994 | Ou |
| 5,401,793 A | 3/1995 | Kobayashi et al. |
| 5,409,777 A | 4/1995 | Kennedy et al. |
| 5,416,140 A | 5/1995 | Columbus et al. |
| 5,418,282 A | 5/1995 | Wiehn |
| 5,421,922 A | 6/1995 | Sperber |
| 5,434,200 A | 7/1995 | Kolker et al. |
| 5,442,023 A | 8/1995 | Argyropoulos et al. |
| 5,461,108 A | 10/1995 | Lewis |
| 5,462,589 A | 10/1995 | Nicholas et al. |
| 5,469,691 A | 11/1995 | Grey et al. |
| 5,470,924 A | 11/1995 | Ryan |
| 5,498,761 A | 3/1996 | Wessling et al. |
| 5,502,088 A | 3/1996 | Hododi |
| 5,507,985 A | 4/1996 | Cadorniga |
| 5,515,792 A | 5/1996 | Bullock et al. |
| 5,549,869 A | 8/1996 | Iwakawa |
| 5,554,429 A | 9/1996 | Iwata et al. |
| 5,582,670 A | 12/1996 | Andersen et al. |
| 5,612,111 A | 3/1997 | Lin |
| 5,616,419 A | 4/1997 | Hsu et al. |
| 5,635,248 A | 6/1997 | Hsu et al. |
| 5,639,800 A | 6/1997 | von Bonin et al. |
| 5,676,905 A | 10/1997 | Andersen et al. |
| 5,715,887 A | 2/1998 | Hosokawa |
| 5,733,633 A | 3/1998 | Lin |
| 5,736,218 A | 4/1998 | Iwata et al. |
| 5,766,525 A | 6/1998 | Andersen et al. |
| 5,769,735 A | 6/1998 | Hosokawa |
| 5,783,543 A | 7/1998 | Fleckenstein et al. |
| 5,786,072 A | 7/1998 | Hsu et al. |
| 5,800,647 A | 9/1998 | Andersen et al. |
| 5,804,641 A | 9/1998 | Iwakawa |
| 5,820,737 A | 10/1998 | Kohn |
| 5,830,548 A | 11/1998 | Andersen et al. |
| 5,843,329 A | 12/1998 | Deetz |
| 5,902,597 A | 5/1999 | Iwakawa et al. |
| 5,910,275 A | 6/1999 | Hausdorf et al. |
| 5,922,379 A | 7/1999 | Wang |
| 5,932,299 A | 8/1999 | Katoot |
| 5,935,675 A | 8/1999 | Hayden et al. |
| 5,945,213 A | 8/1999 | Nagaike et al. |
| 5,968,630 A | 10/1999 | Foster |
| 5,989,781 A | 11/1999 | Idacavage et al. |
| 5,990,224 A | 11/1999 | Raynolds et al. |
| 6,024,784 A | 2/2000 | Buisman et al. |
| 6,030,673 A | 2/2000 | Andersen et al. |
| 6,040,057 A | 3/2000 | Slimak et al. |
| 6,048,431 A | 4/2000 | Clements et al. |
| 6,066,680 A | 5/2000 | Cope |
| 6,083,601 A | 7/2000 | Prince et al. |
| 6,090,479 A | 7/2000 | Shirato et al. |
| 6,099,850 A | 8/2000 | Voris et al. |
| 6,130,268 A | 10/2000 | Murray |
| 6,171,688 B1 | 1/2001 | Zheng et al. |
| 6,180,037 B1 | 1/2001 | Andersen et al. |
| 6,184,285 B1 | 2/2001 | Hatfield et al. |
| 6,240,697 B1 | 6/2001 | Thompson et al. |
| 6,242,041 B1 | 6/2001 | Katoot et al. |
| 6,258,298 B1 | 7/2001 | Blount |
| 6,271,305 B1 | 8/2001 | Rajalingam et al. |
| 6,287,708 B1 | 9/2001 | Viikari et al. |
| 6,290,992 B1 | 9/2001 | Magnuson-Hawkins |
| 6,316,016 B1 | 11/2001 | Iwakawa |
| 6,319,511 B1 | 11/2001 | Van Voris et al. |
| 6,322,853 B1 | 11/2001 | Cuevas |
| 6,342,172 B1 | 1/2002 | Finley |
| 6,348,168 B1 | 2/2002 | Lowrance et al. |
| 6,355,193 B1 | 3/2002 | Stott |
| 6,368,544 B1 | 4/2002 | Owens |
| 6,369,171 B2 | 4/2002 | Dupre et al. |
| 6,383,996 B1 | 5/2002 | Maurin et al. |
| 6,395,824 B1 | 5/2002 | Beutler et al. |
| 6,401,414 B1 | 6/2002 | Steel et al. |
| 6,410,776 B1 | 6/2002 | Roll et al. |
| 6,412,245 B1 | 7/2002 | Lane et al. |
| 6,417,261 B1 | 7/2002 | Maier et al. |
| 6,432,254 B1 | 8/2002 | Black et al. |
| 6,442,912 B1 | 9/2002 | Phillips et al. |
| 6,455,606 B1 | 9/2002 | Kaku et al. |
| 6,461,472 B2 | 10/2002 | Fujii |
| 6,489,392 B1 | 12/2002 | Lappalainen et al. |
| 6,491,850 B1 | 12/2002 | Blount |
| 6,494,438 B1 | 12/2002 | Noirot et al. |
| 6,497,956 B1 | 12/2002 | Phillips et al. |
| 6,528,114 B1 | 3/2003 | Summons |
| 6,534,306 B1 | 3/2003 | Allen |
| 6,538,065 B1 | 3/2003 | Suriano et al. |
| 6,545,729 B1 | 4/2003 | Lowe |
| 6,548,609 B2 | 4/2003 | Ramirez-de-Arellano-Aburto et al. |
| 6,551,537 B2 | 4/2003 | Chen |
| 6,552,109 B1 | 4/2003 | Chen |
| 6,559,270 B1 | 5/2003 | Siclovan et al. |

(56) References Cited

U.S. PATENT DOCUMENTS

| | | |
|---|---|---|
| 6,562,410 B1 | 5/2003 | Mayer et al. |
| 6,572,956 B1 | 6/2003 | Picket et al. |
| 6,590,004 B1 | 7/2003 | Zehner |
| 6,598,700 B1 | 7/2003 | Schroeder |
| 6,607,739 B1 | 8/2003 | Wallo |
| 6,610,409 B2 | 8/2003 | Pickett et al. |
| 6,683,143 B1 | 1/2004 | Mumick et al. |
| 6,686,330 B2 | 2/2004 | Jordan, IV et al. |
| 6,691,485 B1 | 2/2004 | Prokofyev |
| 6,713,156 B1 | 3/2004 | Pauls et al. |
| 6,753,066 B2 | 6/2004 | Eby et al. |
| 6,759,444 B2 | 7/2004 | Brandoli et al. |
| 6,761,177 B1 | 7/2004 | Kedem-Shabi et al. |
| 6,800,352 B1 | 10/2004 | Hejna et al. |
| 6,822,135 B2 | 11/2004 | Soerens et al. |
| 6,844,071 B1 | 1/2005 | Wang et al. |
| 6,846,849 B2 | 1/2005 | Capps |
| 6,863,972 B2 | 3/2005 | Burger et al. |
| 6,868,643 B1 | 3/2005 | Williams |
| 6,890,965 B1 | 5/2005 | Johnson et al. |
| 6,908,677 B2 | 6/2005 | Shoshany et al. |
| 6,911,070 B2 | 6/2005 | Gang |
| 6,936,200 B2 | 8/2005 | Park et al. |
| 6,958,185 B1 | 10/2005 | Zehner |
| 6,962,754 B2 | 11/2005 | Bussi et al. |
| 6,972,277 B2 | 12/2005 | Dietz |
| 7,014,802 B1 | 3/2006 | Eby et al. |
| 7,029,516 B2 | 4/2006 | Campbell et al. |
| 7,063,895 B2 | 6/2006 | Rodrigues et al. |
| 7,097,879 B2 | 8/2006 | Bolton et al. |
| 7,112,626 B1 | 9/2006 | Fickeisen et al. |
| 7,132,023 B2 | 11/2006 | Virtanen et al. |
| 7,141,118 B2 | 11/2006 | Vaerewyck et al. |
| 7,141,195 B2 | 11/2006 | Winterowd et al. |
| 7,153,576 B2 | 12/2006 | Wang et al. |
| 7,160,841 B2 | 1/2007 | Fujita et al. |
| 7,211,318 B2 | 5/2007 | Lee et al. |
| 7,303,642 B2 | 12/2007 | Topolkaraev |
| 7,364,795 B2 | 4/2008 | Daly et al. |
| 7,371,787 B2 | 5/2008 | Preston et al. |
| 7,410,700 B2 | 8/2008 | Wang |
| 7,414,535 B2 | 8/2008 | Hanabusa et al. |
| 7,431,872 B2 | 10/2008 | Dostal et al. |
| 7,473,457 B2 | 1/2009 | Han et al. |
| 7,553,100 B2 | 6/2009 | Muhr-Sweeney |
| 7,595,365 B2 | 9/2009 | Kappes et al. |
| 7,712,265 B2 | 5/2010 | Overmyer, Jr. et al. |
| 7,770,342 B2 | 8/2010 | Marschke |
| 7,790,076 B2 | 9/2010 | Seiter et al. |
| 8,003,082 B2 | 8/2011 | Chaudhuri |
| 8,062,394 B2 | 11/2011 | Gaeta et al. |
| 8,153,261 B2 | 4/2012 | Landon et al. |
| 8,258,066 B2 | 9/2012 | Michaels et al. |
| 8,454,265 B2 | 6/2013 | Carroll |
| 8,510,997 B2 | 8/2013 | Nakamori et al. |
| 8,534,945 B2 | 9/2013 | Muhr-Sweeney |
| 2001/0014386 A1 | 8/2001 | Doppelreiter et al. |
| 2001/0014388 A1 | 8/2001 | Bastioli et al. |
| 2001/0021711 A1 | 9/2001 | Beilfuss et al. |
| 2001/0048974 A1 | 12/2001 | Cai |
| 2002/0065400 A1 | 5/2002 | Raskin et al. |
| 2002/0106504 A1 | 8/2002 | Stott |
| 2002/0115972 A1 | 8/2002 | Dabi et al. |
| 2002/0127374 A1 | 9/2002 | Spratling |
| 2002/0136862 A1 | 9/2002 | Dong et al. |
| 2002/0168503 A1 | 11/2002 | Dong et al. |
| 2002/0174500 A1 | 11/2002 | Micciche et al. |
| 2002/0192272 A1 | 12/2002 | Popp |
| 2003/0017565 A1 | 1/2003 | Echigo et al. |
| 2003/0026976 A1 | 2/2003 | Skrzyniarz et al. |
| 2003/0104135 A1 | 6/2003 | Grantham et al. |
| 2003/0104151 A1 | 6/2003 | Buono et al. |
| 2003/0106699 A1 | 6/2003 | Reiss et al. |
| 2003/0107144 A1 | 6/2003 | Lowe |
| 2003/0116748 A1 | 6/2003 | Haslim |
| 2003/0118814 A1 | 6/2003 | Workman, Jr. et al. |
| 2003/0129384 A1 | 7/2003 | Kalchbrenner |
| 2003/0134015 A1 | 7/2003 | Plaschke |
| 2003/0139712 A1 | 7/2003 | Dodge, II et al. |
| 2003/0150182 A1 | 8/2003 | Chou et al. |
| 2003/0155695 A1 | 8/2003 | Lund et al. |
| 2003/0158344 A1 | 8/2003 | Rodriques et al. |
| 2003/0165669 A1 | 9/2003 | Nowak et al. |
| 2003/0180440 A1 | 9/2003 | Elfersy et al. |
| 2003/0182895 A1 | 10/2003 | Skrzyniarz et al. |
| 2003/0183466 A1 | 10/2003 | Thayer |
| 2003/0192958 A1 | 10/2003 | Miyagi |
| 2003/0203010 A1 | 10/2003 | Wallo |
| 2003/0213168 A1 | 11/2003 | Hesse et al. |
| 2003/0216539 A1 | 11/2003 | Siclovan et al. |
| 2003/0219594 A1 | 11/2003 | Qin et al. |
| 2003/0235601 A1 | 12/2003 | Hallahan |
| 2004/0013757 A1 | 1/2004 | Huang et al. |
| 2004/0023025 A1 | 2/2004 | Magnin |
| 2004/0063367 A1 | 4/2004 | Dodge, II et al. |
| 2004/0065661 A1 | 4/2004 | Wiegner |
| 2004/0066299 A1 | 4/2004 | Hanabusa et al. |
| 2004/0071757 A1 | 4/2004 | Rolf |
| 2004/0074205 A1 | 4/2004 | Stache |
| 2004/0096624 A1 | 5/2004 | Albright |
| 2004/0107484 A1 | 6/2004 | Butter-Jentsch et al. |
| 2004/0108238 A1 | 6/2004 | Maresh |
| 2004/0109853 A1 | 6/2004 | McDaniel |
| 2004/0110657 A1 | 6/2004 | Strothoff |
| 2004/0115354 A1 | 6/2004 | Filippou et al. |
| 2004/0115460 A1 | 6/2004 | Torgovnikov et al. |
| 2004/0116545 A1 | 6/2004 | Jakobstroer et al. |
| 2004/0181180 A1 | 9/2004 | Wood |
| 2004/0234701 A1 | 11/2004 | Caton |
| 2004/0241392 A1 | 12/2004 | Sorrentino |
| 2004/0241540 A1 | 12/2004 | Tsutsumi et al. |
| 2004/0247917 A1 | 12/2004 | Mendes |
| 2004/0253166 A1 | 12/2004 | Kruesi |
| 2004/0253428 A1 | 12/2004 | Wang et al. |
| 2004/0255538 A1 | 12/2004 | Ruhdorfer |
| 2005/0004285 A1 | 1/2005 | Delabroye et al. |
| 2005/0016673 A1 | 1/2005 | Krebs et al. |
| 2005/0038182 A1 | 2/2005 | Hermescec et al. |
| 2005/0042168 A1 | 2/2005 | Kruesi |
| 2005/0042436 A1 | 2/2005 | Glorioso et al. |
| 2005/0051921 A1 | 3/2005 | Winterowd et al. |
| 2005/0054807 A1 | 3/2005 | Winterowd |
| 2005/0112166 A1 | 5/2005 | Hallahan |
| 2005/0118911 A1 | 6/2005 | Nun et al. |
| 2005/0137252 A1 | 6/2005 | Scialdone |
| 2005/0155691 A1 | 7/2005 | Nowak et al. |
| 2005/0158561 A1 | 7/2005 | Wang et al. |
| 2005/0166531 A1 | 8/2005 | McDonald |
| 2005/0169947 A1 | 8/2005 | Korte et al. |
| 2005/0196628 A1 | 9/2005 | Lloyd et al. |
| 2005/0217537 A1 | 10/2005 | Knipe |
| 2005/0230073 A1 | 10/2005 | Hesse et al. |
| 2005/0244521 A1 | 11/2005 | Strickland et al. |
| 2005/0244626 A1 | 11/2005 | Leslie |
| 2005/0250900 A1 | 11/2005 | Stofko |
| 2005/0260369 A1 | 11/2005 | Graf et al. |
| 2005/0263456 A1 | 12/2005 | Cooper et al. |
| 2005/0271599 A1 | 12/2005 | Matthews et al. |
| 2006/0030631 A1 | 2/2006 | Shah et al. |
| 2006/0054290 A1 | 3/2006 | Call |
| 2006/0057300 A1 | 3/2006 | Cui et al. |
| 2006/0061002 A1 | 3/2006 | Huang et al. |
| 2006/0088386 A1 | 4/2006 | Ellis |
| 2006/0100412 A1 | 5/2006 | Schmidt et al. |
| 2006/0110541 A1 | 5/2006 | Russell et al. |
| 2006/0110542 A1 | 5/2006 | Dietz et al. |
| 2006/0113044 A1 | 6/2006 | Virtanen et al. |
| 2006/0124303 A1 | 6/2006 | Nguyen et al. |
| 2006/0128886 A1 | 6/2006 | Winterowd |
| 2006/0142175 A1 | 6/2006 | Haiss et al. |
| 2006/0155013 A1 | 7/2006 | Bumm et al. |
| 2006/0185087 A1 | 8/2006 | Coppens et al. |
| 2006/0188650 A1 | 8/2006 | Sauer |
| 2006/0230707 A1 | 10/2006 | Roe et al. |

(56) References Cited

U.S. PATENT DOCUMENTS

| | | |
|---|---|---|
| 2006/0240079 A1 | 10/2006 | Hallahan et al. |
| 2006/0240243 A1 | 10/2006 | Leslie |
| 2006/0240263 A1 | 10/2006 | Ashmore et al. |
| 2006/0249715 A1 | 11/2006 | Salyer et al. |
| 2006/0254976 A1 | 11/2006 | Cooper |
| 2006/0273477 A1 | 12/2006 | Watt |
| 2006/0293418 A1 | 12/2006 | Matuana et al. |
| 2007/0007686 A1 | 1/2007 | Reid |
| 2007/0010607 A1* | 1/2007 | Smith et al. .......... 524/366 |
| 2007/0020189 A1 | 1/2007 | Maynard |
| 2007/0020476 A1 | 1/2007 | Kintzley et al. |
| 2007/0031919 A1 | 2/2007 | Dunson, Jr. et al. |
| 2007/0105977 A1 | 5/2007 | Gabriel et al. |
| 2007/0110984 A1 | 5/2007 | Reedy |
| 2007/0114621 A1 | 5/2007 | Wisnudel et al. |
| 2007/0122558 A1 | 5/2007 | Gibiat et al. |
| 2007/0128428 A1 | 6/2007 | Moriya et al. |
| 2007/0149409 A1 | 6/2007 | Burnet et al. |
| 2007/0154639 A1 | 7/2007 | Malinger et al. |
| 2007/0169626 A1 | 7/2007 | Sullivan |
| 2007/0193164 A1 | 8/2007 | Gilbert |
| 2007/0193175 A1 | 8/2007 | Hao |
| 2007/0196170 A1 | 8/2007 | McDonald et al. |
| 2007/0204558 A1 | 9/2007 | Carroll |
| 2007/0207222 A1 | 9/2007 | Yu et al. |
| 2007/0227087 A1 | 10/2007 | Nasr et al. |
| 2007/0249805 A1 | 10/2007 | Ittel et al. |
| 2007/0259168 A1 | 11/2007 | Reedy |
| 2007/0261361 A1 | 11/2007 | McDonald |
| 2007/0275101 A1 | 11/2007 | Lu et al. |
| 2007/0298006 A1 | 12/2007 | Tomalia et al. |
| 2008/0029926 A1 | 2/2008 | Steinwender et al. |
| 2008/0053922 A1 | 3/2008 | Honsinger et al. |
| 2008/0081071 A1 | 4/2008 | Sanghvi et al. |
| 2008/0090886 A1* | 4/2008 | Gottsche et al. .......... 514/383 |
| 2008/0096004 A1 | 4/2008 | Crostic |
| 2008/0103281 A1 | 5/2008 | Harvey et al. |
| 2008/0105195 A1 | 5/2008 | Vaerewyck |
| 2008/0171150 A1 | 7/2008 | Hesse et al. |
| 2008/0171231 A1 | 7/2008 | Lopez et al. |
| 2008/0187669 A1* | 8/2008 | Kingma et al. .......... 427/342 |
| 2008/0199682 A1 | 8/2008 | Browne |
| 2008/0207481 A1 | 8/2008 | Meine et al. |
| 2010/0297458 A1 | 11/2010 | Khemani et al. |
| 2012/0276302 A1 | 11/2012 | Thomas et al. |

FOREIGN PATENT DOCUMENTS

| | | |
|---|---|---|
| CA | 1 160 386 | 1/1984 |
| CA | 2 101 833 | 8/1993 |
| CA | 2 125 316 | 6/1994 |
| CA | 2 201 171 | 8/1995 |
| CA | 2 229 005 | 5/1997 |
| CA | 2 318 633 | 9/2000 |
| CA | 2 364 509 A1 | 9/2000 |
| CA | 2 395 455 A1 | 6/2001 |
| CA | 2 472 610 A1 | 7/2003 |
| CA | 2 436 644 A1 | 2/2004 |
| CA | 2 538 263 A1 | 4/2005 |
| CA | 2 240 180 | 1/2008 |
| CA | 2 311 614 C | 5/2009 |
| CA | 2 259 739 A1 | 3/2010 |
| DE | 19704365 A1 | 11/1997 |
| DE | 19839292 A1 | 3/2000 |
| DE | 10061059 A1 | 6/2001 |
| DE | 102005062608 A1 | 7/2007 |
| EP | 0 230 301 A3 | 1/1987 |
| EP | 0 337 474 A2 | 10/1989 |
| EP | 0 567 440 A2 | 10/1993 |
| EP | 0 841 100 A1 | 5/1998 |
| EP | 0 867 770 A1 | 9/1998 |
| EP | 0 949 296 A1 | 10/1999 |
| EP | 1 205 521 A1 | 5/2002 |
| RU | 2067928 C1 | 10/1996 |
| WO | WO 81/00267 | 2/1981 |
| WO | WO 85/01294 A1 | 3/1985 |
| WO | WO 86/07013 A1 | 12/1986 |
| WO | WO 91/13112 A1 | 9/1991 |
| WO | WO 92/11322 A2 | 7/1992 |
| WO | WO 92/21514 | 12/1992 |
| WO | WO 93/09741 | 5/1993 |
| WO | WO 98/47953 A1 | 10/1998 |
| WO | WO 99/01516 A1 | 1/1999 |
| WO | WO 99/03512 A2 | 1/1999 |
| WO | WO 99/24498 A2 | 5/1999 |
| WO | WO 99/32534 A1 | 7/1999 |
| WO | WO 99/61539 A1 | 12/1999 |
| WO | WO 00/05123 A2 | 2/2000 |
| WO | WO 00/05185 A1 | 2/2000 |
| WO | WO 00/27967 A1 | 5/2000 |
| WO | WO 00/52082 A2 | 9/2000 |
| WO | WO 01/05919 A2 | 1/2001 |
| WO | WO 01/46327 A2 | 6/2001 |
| WO | WO 01/56756 A1 | 8/2001 |
| WO | WO 01/96516 A1 | 12/2001 |
| WO | WO 02/29179 A1 | 4/2002 |
| WO | WO 02/100233 A1 | 12/2002 |
| WO | WO 03/013843 A1 | 2/2003 |
| WO | WO 03/037531 A1 | 5/2003 |
| WO | WO 03/056096 A1 | 7/2003 |
| WO | WO 03/074572 A1 | 9/2003 |
| WO | WO 2004/037871 A1 | 5/2004 |
| WO | WO 2004/085102 A2 | 10/2004 |
| WO | WO 2005/037545 A2 | 4/2005 |
| WO | WO 2006/049479 A1 | 5/2006 |
| WO | WO 2006/057558 A1 | 6/2006 |
| WO | WO 2013/009286 A1 | 1/2013 |

OTHER PUBLICATIONS

Materials Research Society Symposium Proceedings, vol. 124, Microwave Processing of Materials, Symposium held Apr. 5-8, 1998, *Microwave Processing at Ontario Hydro Research Division* by S.J. Oda and I.S. Balbaa (cover page, publication page, table of contents p. v, and pp. 302-309).

MSDS, Shaklee Corporation, Get Clean™ Basic H²™, May 21, 2007, 3 pages.

Przewloka et al., *Assessment of commercial low viscosity resins as binders in the wood composite material*, Vintorg, Holz Roh Werkst, (2007) vol. 65 (pp. 209-214).

Rafalski et al., *Small waves against great destroyers, microorganism control in wood using microwave techniques and microwave technology*, Bautenschutz + Bausanierung, (2004) vol. 26, Issue 6 (pp. 37-38, 40-41).

Saito et al., *Microwave-enhanced release of formaldehyde from plywood*, Holzforschung (2004) vol. 58 (pp. 548-551).

Shutov, G.M., *Modification of Wood with Synthetic Resins using Energy of a High-Frequency Electromagnetic Field*, Zesz. Probl. Postepow Nauk Roln. No. 231 (1980) 39-53; English abstract (1 page).

Torgovnikov, G. and Vinden, P., *New microwave Technology and Equipment for Wood Modification*, 2004 AIChE Annual Meeting (2004), 3 pages.

International Search Report (Form PCT/ISA/210) for corresponding International Application No. PCT/US2009/069802 (May 31, 2010).

Written Opinion (Form PCT/ISA/237) for corresponding International Application No. PCT/US2009/069802 (May 31, 2010).

* cited by examiner

PRESERVATION OF WOOD, COMPOSITIONS AND METHODS THEREOF

This application is a continuation of U.S. application Ser. No. 13/142,976 filed Aug. 31, 2011, now issued as U.S. Pat. No. 8,691,340 on Apr. 8, 2014, which is a National Stage Application of PCT/US2009/069802, filed Dec. 30, 2009, which claims benefit of U.S. Provisional Application Ser. No. 61/141,920, filed Dec. 31, 2008, and which applications are incorporated herein by reference. To the extent appropriate, a claim of priority is made to each of the above disclosed applications.

FIELD

The disclosure relates to compositions for wood preservation and methods for using compositions of wood preservation at low pressures or atmospheric pressures.

BACKGROUND

Treatment of wood to extend serviceable life (preservation) has many applications. Treated wood is used in fence posts, utility poles, residential and commercial decking, railroad ties and the like. Additionally, woods that can be treated range from soft woods, such as for example pine, to hard woods such as for example oak or maple.

Methods used to treat wood can be energy and labor intensive. Presently, wood treatment of only sapwood can require subjecting wood to vacuum, followed by high pressure to impregnate wood with treatment compositions. Pressures in the range of 50-250 psig can be used for preservation of wood. Typically, the use of high pressure for wood treatment requires costly pressure containment vessels, controllers and pumps. Associated maintenance costs of those pressure containment vessels and pumps can be high to assure that the pressure vessels maintain integrity (e.g. do not leak) and thus can hold pressure/vacuum. Furthermore, energy requirements of pumps for evacuation and pressurizing the pressure vessels can be high and costly. U.S. Pat. No. 3,968,276 (Allen), U.S. Pat. No. 4,399,195 (Allen) and U.S. Pat. No. 4,433,031 (Allen) disclose wood treatment compositions and methods, and are incorporated herein by reference in their entirety.

With these requirements in mind, there is a need in the wood treatment industry for lower energy consumption methods and lower equipment and equipment maintenance costs for wood preservative applications.

SUMMARY

Embodiments of the present disclosure relate to a composition comprising a pre-polymer and a nonionic surfactant for wood treatment. Further embodiments include a method for treating both sapwood and heartwood using said compositions.

Some embodiments in accordance with the present disclosure include a composition for preserving wood comprising:
  a prepolymer comprising from about 4 wt % to about 20 wt % of the total composition; and
  a nonionic surfactant mixture comprising alkylpolyglycosides and ethoxylated alcohols from about 0.1 wt % to about 1.0 wt % of the total composition;
  wherein the pre-polymer has a weight average molecular weight ($MW_w$) in the range of from about 125 to about 400 such that the pre-polymer impregnates wood with pressures from about ambient atmospheric pressure to about 15 psig.

Other embodiments include a method of preserving wood comprising:
  (a) contacting a wood with a solution of a pre-polymer and nonionic surfactant; and
  (b) curing the wood that has been contacted with the solution of prepolymer and nonionic surfactant; wherein
  the method is conducted from about ambient atmospheric pressure to about 15 psig;
  the solution of prepolymer and nonionic surfactant comprises from about 2 wt % to about 20 wt % of prepolymer of the total weight of solution of the prepolymer and nonionic surfactant; and
  the curing step comprises heating the wood at temperatures above 25° C.

Composition and methods of the present disclosure allow for reduced energy expenditures for treatment of wood when compared with vacuum/pressure treatment methods presently used in the wood preservation industry. Certain embodiments of the present disclosure require simpler, less expensive equipment for affecting wood preservation, in that vacuum and pressure equipment can be eliminated, replaced for example, by fluid containing vessels and/or spray equipment that are operated at ambient or low pressure (for example, but not limited to 5 psig). Methods of the present disclosure can also reduce the inventory of treated wood on site at wood treatment centers.

DETAILED DESCRIPTION OF ILLUSTRATIVE EMBODIMENTS

As used herein, the following definitions define the stated term:

A "prepolymer" is a composition of relatively low weight average molecular weight ($MW_w$) which can be polymerized to produce a polymer. The prepolymer is typically soluble in water or a suitable solvent. Though not limiting, an example of a prepolymer can be the reaction product of formaldehyde and phenol with a weight average molecular weight ($MW_w$) of from about 125 to about 400.

The term "impregnation" refers to a point in the preservation process of the present disclosure whereby the specific wood being treated can reach a refusal point whereby the wood cannot accept any further material under the given process and composition parameters.

The term "curing" refers to polymerization or crosslinking of a prepolymer by a method that induces polymerization or crosslinking of the pre-polymer. Curing can be induced by a combination of time and temperature for a temperature dependent polymerization system. Curing can induce polymerization with other like prepolymers. Curing can also be polymerization with pre-polymers and other reactive sites, such as reactive sites on cellulose. In some cases, curing can be a combination of polymerization with other like prepolymers and polymerization with reactive sites.

The term "low pressure" refers to process pressures between about atmospheric pressure and about 24 psig.

The term "preservative" refers to any material applied to the wood which can act as an insect repellant, a microorganism repellant, an insecticide, fire retardant, rot retardant, fireproofing agent, a biocidal agent or combinations thereof.

Prepolymer

The prepolymer for wood preservation can be soluble in a suitable solvent. From an economic perspective and because water can be easily accessible at wood treatment sites, the prepolymer for treatment of wood in some embodiments can be a water soluble prepolymer composition. Solutions of compositions for wood preservation of the present disclosure can contain from about 2.0 wt % to about 20 wt % prepolymer. In other embodiments in accordance with the present disclosure compositions for wood preservation of the present disclosure can contain about 15 wt %, about 12 wt %, about 10 wt %, about 8 wt %, about 6 wt %, about 5 wt %, about 4 wt % or even about 3 wt % prepolymer, depending upon the density of wood being treated, the physical and chemical characteristics of the prepolymer being used and the desired impregnation level of the preservative.

The weight average molecular weight ($MW_w$) of the prepolymer can be adjusted such that when the prepolymer solution contacts the wood to be treated, the prepolymer can impregnate the wood to an effective level to provide desired wood preservation. Generally, prepolymer compositions with low viscosity can be advantageous for ease of use. It can be advantageous in some embodiments of the present disclosure to provide a mixture of prepolymers to achieve a specific outcome, such as for example, but not limited to, preserving green lumber.

In some embodiments the prepolymer can be a condensation prepolymer. Examples of condensation prepolymers in accordance with the present disclosure include, but are not limited to, condensation prepolymers of urea derivatives and formaldehyde. The specific prepolymer resins that can be used include, but are not limited to urea formaldehyde, urea melamine formaldehyde, urea furfural, phenol formaldehyde or mixtures thereof. In other embodiments the prepolymer can be a condensation prepolymer of melamine derivatives and formaldehyde. In yet other embodiments the prepolymer can be a condensation prepolymer of phenolic derivatives and formaldehyde.

In other embodiments, the prepolymer comprises a phenol-formaldehyde prepolymer with a weight average molecular weight ($MW_w$) in the range of from about 125 to about 400. In other embodiments the weight average molecular weight ($MW_w$) can be less than about 350, less than about 300, less than about 250, less than about 200, or even less than about 140.

Nonionic Surfactants

Suitable nonionic surfactants for use in accordance with the present disclosure include alkoxylated surfactants in combination with alkyl polyglycosides. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as "DEHYPON LS-54" (R-$(EO)_5(PO)_4$) and DEHYPON LS-36" (R-$(EO)_3(PO)_6$); and capped alcohol alkoxylates, such as "PLURAFAC LF221" and "TEGOTEN EC11"; mixtures thereof, or the like.

Nonionic surfactant mixtures employed in compositions of the present disclosure can be at concentrations higher than those conventionally employed as surfactants. For example, concentrated compositions can include from about 0.01 wt % to about 1.0 wt % of nonionic surfactants. In other embodiments, nonionic surfactant mixtures can include up to about 0.9 wt %, about 0.7 wt %, about 0.5 wt %, about 0.3 wt %, about 0.1 wt %, about 0.08 wt %, about 0.06 wt %, about 0.04 wt %, or even about 0.02 wt % of the composition.

Ethoxylated alcohols useful in some embodiments of the present disclosure include C12-C16 ethoxylated alcohols, "ALEX 12.0", "ALEX 4.0", "ALEX 6.0", "ALFONIC 1216-1.3", "ALFONIC 1216-22", "BEROL 175", "DEHYDROL LSS 5.5", "ETHONIC 1214-2", "ETHONIC 1214-6.5", "GENAPOL 24/50", "GENAPOL 24L50", "GENAPOL 26L3", "GENAPOL 26L80", "GENAPOL LA 060", "GENAPOL UD 030S", "MERPOL HCS" and "NEONOL P 12-16-3."

In some embodiments of the present disclosure alkylpolyglycosides such as D-glucopyranose, oligomeric, C10-C 16 alkyl glycosides and D-glucopyranose, oligomeric, decyl octyl glycosides (CAS—110615-47-9), linear alcohol alkoxylates (CAS—37251-67-5; 68551-12-2), and pareth 25-7 (CAS—68131-39-5), or mixtures thereof, can be used in surfactant mixtures of the compositions.

Examples of pareth 25-7 can include "ADEKATOL SO 160", "AE 25-15A", "AEO 40", "AEO 9", "ALFONIC 1012-40", "ANAPOE C13E8", "BIO-SOFT EN 600", "C12-15 PARETH 3", "C12-15 PARETH-9", "DOBANOL 25-7", "DOBANOX 25-7", "EMERIST 7232", "EMPILAN KCL 9", "GENAPOL 26L45", "GENAPOL LA 050", "IMBENTIM C 125/094", "LIALET 125/5", "MARLIPAL 025/70", "MULSIFAN RT 203/80", "NEODOL 25-12", "NEODOL 25-9" and "NEONOL P 1215-3."

Additionally, examples of linear alcohol alkoxylates can include 2-methyl oxirane monodecyl ether, methyl oxirane monodecyl ether, ethylene oxide/propylene oxide copolymer monodecyl ether, polyethylene/polypropylene glycol monodecyl ether, "BIODAC 11009", "BIODAC OP 1", "EMALEX DAPE 0203", "EMALEX DAPE 0230", "ETHOX 1437", "ETHOX 1449", "EUSAPON LD 6031", "FINESURF ELP 1608B", "LUTENSOL XL 60", "NOIGEN XL 60" and "PEGNOL D 218."

Methods of Wood Preservation.

The prepolymer nonionic surfactant composition can be brought into contact with the wood to be treated using many different methods. The prepolymer nonionic surfactant composition can be sprayed onto the wood, dripped onto the wood, curtain-coated on the wood, atomized, sonicated, applied with a reciprocating arm (similar in action to a windshield wiper), wiped, and combinations thereof. In other embodiments of the method of wood treatment using the compositions of the present disclosure, the prepolymer nonionic surfactant compositions can be charged to a tank and the wood to be treated can be submerged in the prepolymer nonionic surfactant composition in the tank to allow intimate contact of the wood with the prepolymer nonionic surfactant composition treatment bath. The treatment bath can be stirred to ensure contact of the prepolymer nonionic surfactant mixture with the wood. The wood to be treated can be submerged in the bath without stirring. Alternatively, the wood to be treated can be partially submerged into the prepolymer nonionic surfactant mixture contacting bath with the wood rotated such that all surfaces of the wood are contacted with prepolymer nonionic surfactant mixture.

The wood treated with prepolymer nonionic surfactant compositions in accordance with the present application can be subjected to low pressure, for example, but not limited to pressures between about atmospheric and about 24 psig. In other embodiments, the treated wood can be subjected to pressures between about atmospheric and about 22 psig, between about atmospheric and about 20 psig, between about atmospheric and about 18 psig, between about atmospheric and about 16 psig, between about atmospheric and about 14 psig, between about atmospheric and about 12 psig, between about atmospheric and about 10 psig, between about atmospheric and about 8 psig, between about atmospheric and about 7 psig, between about atmospheric and about 6 psig, between about atmospheric and about 5 psig, between about atmospheric and about 4 psig, between about atmospheric and about 3 psig, between about atmospheric and about 2 psig or even in some cases between about atmospheric and about 1 psig.

Other methods of contacting wood to be preserved with the prepolymer nonionic surfactant mixture can include, but are not limited to, contacting only a portion of the wood to be treated with the prepolymer nonionic surfactant mixture. In one embodiment, such contact with portions of the wood can include dipping one or both ends of a utility pole or fence post vertically into a bath of prepolymer nonionic surfactant mixture. This method can preferentially treat and preserve the portion of the utility pole or fence post that would be buried and in contact with the ground. This preferential end-dipping application of preservative presents problem to applications that require vacuum and/or pressure, as the vacuum/pressurized treatment systems are horizontally disposed. Dipping the end of very long posts or telephone poles (e.g. 10, 30 or 100 feet long) would require major modifications to the horizontally disposed systems now used that require vacuum and high pressure for wood treatment.

The method of contacting wood to be preserved with the prepolymer nonionic surfactant mixture can be achieved by preparing aqueous solutions of prepolymer nonionic surfactant compositions. Measures can be taken to avoid curing the prepolymer solution or the prepolymer nonionic surfactant mixture composition before contact with the wood to be treated. Such measures include avoiding subjecting the prepolymer solution or the prepolymer nonionic surfactant mixture composition to temperatures over 40° F. for extended periods of time.

Curing

The resulting wood that has been contacted with the prepolymer nonionic surfactant mixture can be cured by a combination of time and temperature which has been chosen to optimize the particular polymer and size of wood being treated. For example, a 6 inch×6 inch fence post would take more time to cure than a 1 inch×6 inch board. This is due to the fact that the fence post is thicker than the board and can absorb more prepolymer, requiring a longer time or higher temperature to cure. The cure time can also be dependent upon the original water content of the wood before contact with the prepolymer mixture.

The treated wood can be cured by directly subjecting the treated wood to steam. In other embodiments, the treated wood can be cured by subjecting the treated wood to heat in an oven. Typically oven temperatures used to cure the treated wood include from about 110° F. to about 140° F. In some instances, the treated wood can be partially cured using steam or heated in an oven, and the remaining uncured treated wood can cure over long periods of time (e.g. days or months) in use at ambient temperature of about 72° F.

In some embodiments, curing the prepolymer nonionic surfactant composition can cause polymerization or crosslinking of the prepolymer composition with itself. For example, but not meant to be limiting, a phenol formaldehyde prepolymer can form a phenolic polymer. In other embodiments, curing can cause polymerization of the composition with sites on the wood which can be susceptible to reaction with the prepolymer. Sites on the wood which can be susceptible to polyermization include, but are not limited to, for example, hydroxyl groups on cellulose that can form ether linkages with the prepolymer or polymerized prepolymer. In yet other embodiments in accordance with the present disclosure curing can cause a combination of polymerization or crosslinking of the prepolymer with itself in combination with reaction of the prepolymer with sites on the wood which can be susceptible to reaction with the prepolymer nonionic surfactant composition.

It may be desirable that in some embodiments cure of the prepolymer nonionic surfactant composition is only partially performed using any of the means described above. The curing can be conducted at the preservation facility such that only a portion of the prepolymer is cured, and the remaining uncured prepolymer will be cured at ambient temperature as the preserved wood is put into use, for example, as a utility pole. This would allow for a shorter cure time at the preservation facility, thus reducing the time required for processing the preserved wood, while still allowing for ultimate full curing at ambient temperature of the preserved wood over a longer period of time once in the end use environment.

Other Benefits

Preserving wood with prepolymer compositions of the present disclosure also imparts dimensional stability, reduces hygroscopicity and gives protection from weathering. In some embodiments preserved wood with prepolymer compositions increases hardness, compression strength and modulus. The preserved wood with cured prepolymer can additionally have increased fastener holding power, such as, for example railroad spikes and other fasteners. Only a minor decrease in tensile strength can be observed in some species of wood. For example, the modulus of elasticity of phenol-formaldehyde treated wood increases from about 35 to about 40%. The rupture of phenol-formaldehyde treated wood increases from about 27 to about 43%, with a tensile strength decrease of only about 10%.

EXAMPLES

In Comparative Examples 1-2 and Example 1, each experiment was conducted using three Southern Yellow Pine (SYP) boards, at approximately 20% moisture content (one board was 1.5 inches thick×15.5 inches long×5.5 inches wide; two boards were 1.5 inches thick×15.5 inches long×3.25 inches wide).

Comparative Example 1

To 20 parts by volume of prepolymer solution (phenol-formaldehyde prepolymer solution with 70 wt % solids; weight average molecular weight ($MW_w$) in the range of 140-350 and a viscosity of 110 cps) was added 180 parts by volume of water. The boards were loaded into a pressure tank measuring approximately 2 foot length×1 foot diameter. A sufficient amount of prepolymer solution was added to the tank and boards to completely submerge the boards. The tank was closed and pressurized to 5 psig. After 30 minutes the tank pressure was relieved and the boards were removed and weighed. The dry weight of the prepolymer remaining in the boards was calculated using the theoretical percent solids of the prepolymer solution. The result dry weight for all three boards was 0.346 lbs of prepolymer/ft$^3$ retention.

Comparative Example 2

Comparative Example 2 was a duplicate run of the procedure described for Comparative Example 1. The result dry weight for all three boards was 0.355 lbs of prepolymer/ft$^3$ retention.

Example 1

The procedure described in Comparative Example 1 was repeated for Example 1, with the exception that 1 part by volume of nonionic surfactant aqueous solution containing deionized water (maximum about 72 wt %), pareth 25-7 (maximum about 22 wt %), linear alcohol ethloxylates (maximum about 9 wt %), "DOWICIL 75®" (maximum about 0.15 wt %), HCl (maximum about 0.05 wt %), butyrated hydroxytoluene (maximum about 0.015 wt %), D & C7 Green #5 (maximum about 0.002 wt %) and methylparaben (maximum about 0.001 wt %) was added to the pre-polymer solution. The result dry weight for all three boards was 0.47 lbs of prepolymer-surfactant/board ft$^3$ retention.

Examples 2-6

To 20 parts of prepolymer (phenol-formaldehyde prepolymer solution with 70 wt % solids; weight average molecular weight (MW$_w$)=140-350 and a viscosity of 110 cps) was added 180 parts of water and 1.0 part of nonionic surfactant mixture containing alkylpolyglycoside (between 20-30% wt; CAS #110615-47-9 and CAS #68515-73-1) and ethoxylated alcohol (between 10-15% wt; CAS #68551-12-2), with the remainder being water. Twenty-five boards (green poplar; each board 1 inch×6 inch×16 ft; total of 0.67 ft$^3$) were placed in a steel tank (approximate dimensions of 26 ft.×3.5 ft×3.5 ft). The boards were arranged such that boards designated with lower numbers (for example: Example 2; 4 boards) were closest to the bottom of the tank, with boards designated with higher numbers (for example: Example 6; 5 boards) being closest to the top of the tank. The ensuing prepolymer nonionic surfactant mixture composition was charged to the steel tank, submerging the boards in the prepolymer nonionic surfactant mixture composition. The boards were submerged in the solution for approximately 2 hours at atmospheric pressure. Table 1 lists the average wt % retention of prepolymer per cubic foot of board (on a dry basis).

TABLE 1

| Example | No. of boards | Weight gain (wet, lbs) | Board ft$^3$ | Retention of prepolymer; dry (lbs/ft$^3$) |
|---|---|---|---|---|
| Ex. 2 | 4 | 8.4 | 2.68 | 0.22 |
| Ex. 3 | 4 | 7.6 | 2.68 | 0.20 |
| Ex. 4 | 4 | 6.2 | 2.68 | 0.16 |
| Ex. 5 | 4 | 5.4 | 2.68 | 0.14 |
| Ex. 6 | 5 | 7.2 | 3.35 | 0.15 |

Examples 7-13

The procedure described for Examples 2-6 above was used with the exception that the green poplar boards were replaced with debarked southern yellow pine (Air Dried) poles as described in Table 2.

TABLE 2

| Example | Size (diameter × length in inches) | Weight gain (wet, lbs) | Pole ft$^3$ | Retention of prepolymer; dry (lbs/ft$^3$) |
|---|---|---|---|---|
| Ex. 7 | 7 × 96 | 15.2 | 2.13 | 0.50 |
| Ex. 9 | 4 × 84 | 3.4 | 0.61 | 0.39 |
| Ex. 9 | 3.5 × 96 | 7.6 | 0.53 | 1.00 |
| Ex. 10 | 4.5 × 84 | 3.4 | 0.77 | 0.31 |
| Ex. 11 | 7.5 × 96 | 10.4 | 2.45 | 0.30 |
| Ex. 12 | 3.5 × 96 | 9.2 | 0.53 | 1.22 |
| Ex. 13 | 4 × 96 | 7.8 | 0.70 | 0.78 |

Examples 14-16

The procedure described for Examples 2-6 above was used with the exception that the green poplar boards were replaced with green, debarked southern yellow pine poles as described in Table 3.

TABLE 3

| Example | Size (diameter × length in inches) | Weight gain (wet, lbs) | Pole ft$^3$ | Retention of prepolymer; dry (lbs/ft$^3$) |
|---|---|---|---|---|
| Ex. 14 | 4.5 × 84 | 0.6 | 0.77 | 0.05 |
| Ex. 15 | 4 × 84 | 0.6 | 0.61 | 0.07 |
| Ex. 16 | 4.5 × 84 | 0.6 | 0.77 | 0.02 |

Examples 17-20

The procedure described for Examples 2-6 above was used with the exception that the green poplar boards were replaced with southern yellow pine boards (air dried) as described in Table 4.

TABLE 4

| Designation | Size (width × height × length in inches) * | Weight gain (wet, lbs) | Board ft$^3$ | Retention of prepolymer; dry (lbs/ft$^3$) |
|---|---|---|---|---|
| Ex. 17 | 3.5 × 9 × 23 | 7.6 | 0.42 | 1.27 |
| Ex. 18 | 3.5 × 9 × 23 | 5.2 | 0.42 | 0.87 |
| Ex. 19 | 3.5 × 9 × 23 | 7.0 | 0.42 | 1.17 |
| Ex. 20 | 3.5 × 9 × 23 | 7.6 | 0.42 | 1.27 |

* These pieces had a considerable percentage of heartwood.

Examples 21-26

The procedure described for Examples 2-6 above was used with the exception that the green poplar boards were replaced with green railroad ties as described in Table 5.

TABLE 5

| Example | Species | Size (width × height × length in inches) | Weight gain (wet, lbs) | Board ft$^3$ | Retention of prepolymer; dry (lbs/ft$^3$) |
|---|---|---|---|---|---|
| Ex. 21 | White Oak | 6 × 8 × 105.5 | 2.8 | 2.93 | 0.07 |
| Ex. 22 | White Oak | 6 × 6 × 107.5 | 1.0 | 2.24 | 0.03 |
| Ex. 23 | Hickory | 6 × 6 × 107.5 | 1.6 | 2.24 | 0.05 |
| Ex. 24 | Hickory | 6 × 6 × 107 | 1.4 | 2.23 | 0.04 |
| Ex. 25 | Red oak | 6 × 6 × 101.5 | 0.8 | 2.12 | 0.03 |
| Ex. 26 | Red oak | 6 × 8 × 112 | 0.4 | 3.11 | 0.01 |

Examples 27-35

The procedure described for Examples 2-6 above was used with the exception that the green poplar boards were replaced with green railroad tie side boards as described in Table 6.

TABLE 6

| Example | Species | Size (width × height × length in inches) | Weight gain (wet, lbs) | Board ft³ | Retention of prepolymer; dry (lbs/ft³) |
|---|---|---|---|---|---|
| Ex. 27 | Red Oak | 1 × 9 × 105.5 | 1.4 | 0.55 | 0.18 |
| Ex. 28 | Hickory | 1 × 9 × 116.5 | 0.4 | 0.61 | 0.05 |
| Ex. 29 | Hickory | 1 × 9 × 114.5 | 0.6 | 0.60 | 0.07 |
| Ex. 30 | Red Oak | 1 × 6 × 111 | 0.4 | 0.39 | 0.07 |
| Ex. 31 | Red Oak | 1 × 6 × 107 | 1.4 | 0.37 | 0.26 |
| Ex. 32 | Red Oak | 1 × 6.5 × 111 | 0.4 | 0.42 | 0.07 |
| Ex. 33 | Red Oak | 1 × 6 × 107 | 1.6 | 0.37 | 0.30 |
| Ex. 34 | Red Oak | 1 × 6.5 × 105 | 1.2 | 0.40 | 0.21 |
| Ex. 35 | Red Oak | 1 × 6 × 119 | 1.2 | 0.41 | 0.20 |

We claim:

1. A composition for preserving wood comprising:
a prepolymer comprising from about 4 wt % to about 20 wt % of the total composition; and
about 0.01 to about 1.0 wt % of a nonionic surfactant mixture comprising alkylpolyglycosides and ethoxylated alcohols;
wherein the pre-polymer has weight average molecular weight ($MW_w$) in the range of from about 125 to about 400 such that the pre-polymer impregnates wood with pressures from about atmospheric to about 15 psig.

2. The composition of claim 1 wherein the pre-polymer comprises a phenol-formaldehyde prepolymer.

3. The composition of claim 1 wherein the nonionic surfactant mixture comprises monodecyl ether derivatives of linear alkoxylates and C12-C15 ethoxylated alcohols.

4. The composition of claim 1 wherein the pre-polymer comprises a water soluble prepolymer in aqueous base.

5. The composition of claim 1 wherein the pre-polymer has weight average molecular weight ($MW_w$) in the range of from about 125 to about 300 such that the pre-polymer impregnates the wood with pressures from about atmospheric to about 10 psig.

6. The composition of claim 1 wherein the pre-polymer has weight average molecular weight ($MW_w$) in the range of from about 125 to about 200 such that the pre-polymer impregnates the wood with pressures from about atmospheric to about 5 psig.

7. The composition of claim 1 wherein the pre-polymer has weight average molecular weight ($MW_w$) in the range of from about 125 to about 140 such that the pre-polymer impregnates the wood with pressures from about atmospheric to about 1 psig.

8. The composition of claim 1 wherein the pre-polymer comprises from about 5 wt % to about 10 wt % of the composition.

* * * * *